United States Patent
Van Dijk

(10) Patent No.: US 11,311,451 B2
(45) Date of Patent: Apr. 26, 2022

(54) DEVICE FOR PERIODONTAL CLEANING AND A METHOD OF CONTROLLING A DEVICE PERIODONTAL CLEANING

(71) Applicant: GUM IRRIGATOR B.V., Groningen (NL)

(72) Inventor: Lolke Van Dijk, Winsum (NL)

(73) Assignee: GUM IRRIGATOR B.V., Groningen (NL)

( * ) Notice: Subject to any disclaimer, the term of this patent is extended or adjusted under 35 U.S.C. 154(b) by 439 days.

(21) Appl. No.: 15/735,402

(22) PCT Filed: Jun. 10, 2016

(86) PCT No.: PCT/EP2016/063344
§ 371 (c)(1),
(2) Date: Dec. 11, 2017

(87) PCT Pub. No.: WO2016/198632
PCT Pub. Date: Dec. 15, 2016

(65) Prior Publication Data
US 2018/0153762 A1  Jun. 7, 2018

(30) Foreign Application Priority Data

Jun. 12, 2015  (NL) ..................... 2014963

(51) Int. Cl.
*A61H 13/00* (2006.01)
*A61C 17/08* (2006.01)
(Continued)

(52) U.S. Cl.
CPC ......... *A61H 13/005* (2013.01); *A61C 1/0015* (2013.01); *A61C 1/0092* (2013.01);
(Continued)

(58) Field of Classification Search
CPC ...... A61H 9/00; A61H 9/0007; A61H 9/0021; A61H 9/0028; A61H 9/0042; A61H 13/00;
(Continued)

(56) References Cited

U.S. PATENT DOCUMENTS

| 5,145,367 A | 9/1992 | Kasten | |
|---|---|---|---|
| 2003/0219696 A1* | 11/2003 | Moreland | A61C 17/08 433/95 |
| 2008/0145816 A1* | 6/2008 | Hershey | A61C 17/08 433/95 |
| 2010/0203470 A1* | 8/2010 | Sidhu | A61C 17/08 433/92 |

(Continued)

FOREIGN PATENT DOCUMENTS

| DE | 3738811 A1 * | 8/1988 | ......... A61C 17/0208 |
|---|---|---|---|
| WO | 2007025244 A2 | 3/2007 | |

(Continued)

*Primary Examiner* — Margaret M Luarca
*Assistant Examiner* — Cana A Gallegos
(74) *Attorney, Agent, or Firm* — Steven M. Koehler; Westman, Champlin & Koehler, P. A.

(57) ABSTRACT

A periodontal cleaning device, including a cleaning head having a fluid outlet for releasing a cleaning fluid and a suction member for suction of a waste fluid, a cleaning fluid source, connected to the fluid outlet, a controllable suction device connected to the suction member, fluid feeding device for controlling a flow of the cleaning fluid from the cleaning fluid source to the fluid outlet. The periodontal cleaning device further has a control unit, arranged for controlling the controllable suction device in generating a vacuum pulse in the suction member, controlling controllable fluid feeding device in generating a fluid flow pulse in the fluid outlet in response to the vacuum pulse, and controlling the controllable suction device in generating a subsequent vacuum pulse in the suction member, and introducing a time period between the cleaning fluid flow pulse and the subsequent vacuum pulse in the suction member.

21 Claims, 5 Drawing Sheets

(51) Int. Cl.
*A61C 17/02* (2006.01)
*A61M 1/00* (2006.01)
*A61C 1/00* (2006.01)
*A61C 17/028* (2006.01)

(52) U.S. Cl.
CPC ...... *A61C 17/0202* (2013.01); *A61C 17/0208* (2013.01); *A61C 17/028* (2013.01); *A61C 17/08* (2019.05); *A61M 1/0001* (2013.01); *A61M 1/79* (2021.05)

(58) Field of Classification Search
CPC ...... A61H 13/005; A61C 17/00; A61C 17/02; A61C 17/0202; A61C 17/0208; A61C 17/0211; A61C 17/04; A61C 17/06; A61C 17/08; A61C 17/12; A61C 17/135
See application file for complete search history.

(56) References Cited

U.S. PATENT DOCUMENTS

| | | | |
|---|---|---|---|
| 2013/0164705 A1 | 6/2013 | Tanaka et al. | |
| 2015/0250570 A1* | 9/2015 | Persons | A61C 17/0202 433/80 |
| 2016/0038348 A1* | 2/2016 | Booth | A46B 15/0081 433/136 |
| 2017/0238693 A1* | 8/2017 | Sissons | A46B 5/026 |

FOREIGN PATENT DOCUMENTS

| | | | | |
|---|---|---|---|---|
| WO | WO-2007025244 A2 * | 3/2007 | | A61L 2/084 |
| WO | 2015059707 A1 | 4/2015 | | |
| WO | WO-2015059707 A1 * | 4/2015 | | A61C 17/0208 |

* cited by examiner

DEVICE FOR PERIODONTAL CLEANING AND A METHOD OF CONTROLLING A DEVICE PERIODONTAL CLEANING

FIELD OF THE INVENTION

The invention relates to a device for periodontal cleaning and a method of controlling a device for periodontal cleaning.

BACKGROUND OF THE INVENTION

Periodontal cleaning of pockets in gums of human or animal subjects can be aimed at both treatment of gum illnesses or at prevention thereof. Such treatment can comprises introduction of cleaning fluids in the subject mouth, especially in crevices between teeth and gums, the pockets where bacteria causing such illnesses may reside and thrive. The introduced cleaning fluid rinses the pockets. The introduced cleaning fluid can also comprise antibiotic or other medicaments to counteract any pathological condition of the gums. The cleaning fluid can be introduced for example by high pressure such that it can permeate into said pockets. Permeation of said fluid however appears to be insufficient, and the high pressure introduction of the fluid involves spilling of the fluid causing unhygienic situations.

Alternatively, from U.S. Pat. No. 5,145,367 a vacuum instrument is known for dental hygiene and dental treatment, intended for periodontal treatment of tooth pockets. The instrument according to U.S. Pat. No. 5,145,367 has an elastic suction cap which can produce a sealed vacuum over the gum pockets and interdental crevices. A treatment liquid is supplied to the suction cap and removed by the suction. Intermittent application of the vacuum produces a pumping action, which through likewise intermittent rinsing results in cleaning of the pockets as far as the base of it. The intermittent application of the vacuum together with the introduction of cleaning fluid however causes an uncontrolled amount of cleaning fluid to be sucked in before it has properly performed its cleaning and antibacterial action. Moreover, the suction cap may not provide sufficient low pressure, i.e. vacuum for the cleaning fluid to sufficiently penetrate the tooth crevices and gum pockets. This occurs especially when there is an overlap between applying the vacuum to the cup and releasing the cleaning fluid. Moreover the uncontrolled amount of cleaning fluid causes spilling of the fluid, contamination of the clean rinsing fluid, thus resulting in unhygienic situations.

SUMMARY OF THE INVENTION

It is therefore an object of the invention to provide a periodontal cleaning with improved action and improved hygiene.

The object is achieved in a periodontal cleaning device, comprising a cleaning head having a fluid outlet for releasing a cleaning fluid and a suction member for suction of a waste fluid, a cleaning fluid source, connected to the fluid outlet, controllable suction means connected to the suction member via a suction line, controllable fluid feeding means for controlling a flow of the cleaning fluid from the cleaning fluid source to the fluid outlet. The periodontal cleaning device further has a control unit, the control unit being arranged for controlling the controllable suction means in generating a vacuum pulse in the suction member, controlling controllable fluid feeding means in generating a fluid flow pulse in the fluid outlet in response to the vacuum pulse, and controlling the controllable suction means in generating a subsequent vacuum pulse in the suction member, and the control unit being arranged for pausing a predetermined time period between the generating the cleaning fluid flow pulse in the fluid outlet and the generating the subsequent vacuum pulse in the suction member.

The cleaning head can be applied to periodontal areas of a subjects mouth, more specifically on the crevices between the teeth and the gums, onto the pockets that require cleaning. The pausing a predetermined time period between the cleaning fluid flow pulse and the subsequent vacuum pulse in the suction member allows for the cleaning fluid to penetrate the pockets where it can perform its cleaning action. It further allows the removal of the fluid content of the pockets, containing many pathogenic enzymes from microorganisms and leucocytes with any plaque and/or other contamination to be softened and be contained by the cleaning fluid and subsequently drained from the crevices and pockets. The cleaning fluid supply and suction of waste fluid have completely separate paths, so waste fluid cannot enter the cleaning fluid supply line. This allows hygienic use of the device.

The subsequent vacuum pulse allows the waste fluid, i.e. the cleaning fluid with contaminants soaked therein, to be effectively removed from the subjects mouth. It has been found that the pausing is very effective and improves the performance of the periodontal cleaning significantly. Moreover, the suction pulse after the pausing allows for removal of the waste fluid, thereby preventing contaminants in the waste fluid contaminating and/or infecting other parts of the subjects mouth. This improves a subject's comfort during the cleaning, as the waste fluid no longer is drained through the subjects mouth.

The fluid outlet for releasing a cleaning fluid is coaxially centered within the suction member. Thus the cleaning fluid can be injected in the centre of the periodontal area where the suction member is positioned.

In an embodiment, the fluid outlet resiliently extends beyond the suction member. This allows usage of the periodontal cleaning device by an individual subject himself. By rubbing or touching the gums with the fluid outlet, the suction cup can be stabilized easily and the subject is also able to establish the most sensitive areas to apply the cleaning action of the periodontal cleaning device. Thus effective usage of the periodontal cleaning device at home independently from a dentist or dental hygienist is possible.

In an embodiment, the predetermined time period is in a range of 150 to 500 ms, and preferably in a time range of 200 to 300 ms. A more preferable predetermined time period is in a range of 240-260 ms. It has been experimentally established that with a pause duration of approximately 250 ms a relatively low vacuum i.e. negative- or underpressure is required for the vacuum pulse. Such negative pressure may be in the order of 35 mm HG. Also the amount of cleaning fluid and pressure for applying the cleaning fluid can be low. With vacuum pulse duration and cleaning fluid pulse duration of also approximately 250 ms a cleaning cycle of vacuum pulse, cleaning fluid pulse and pause lasts approximately 750 ms. For sufficient cleaning of a pocket, 6-13 cycles may be required, thus a total cleaning time in the order of 4.5 s to 10 s can be achieved.

In an embodiment, the control unit is arranged for generating a cleaning fluid flow pulse in the fluid outlet in response to the vacuum pulse between the generating of a vacuum pulse. In other words, there is no overlap between the vacuum pulse and the cleaning fluid flow pulse. This prevents cleaning fluid to be sucked away from the subjects mouth before it can do its function of periodontally cleaning the subjects mouth.

In an embodiment, the generating a cleaning fluid flow pulse involves generating a predetermined amount of cleaning fluid. This ensures a proper dosage of cleaning fluid and prevents unnecessary usage or spilling thereof.

In an embodiment, the controllable fluid feeding means comprise a fluid pump between the cleaning fluid source and the fluid outlet. The fluid pump allows effective control and generation of the cleaning fluid flow pulse by switching the fluid pump on and off at appropriate times.

In an embodiment, the controllable fluid feeding means comprise a first controllable valve between the cleaning fluid source and the fluid outlet. The first controllable valve has a forward flow in the direction towards the fluid outlet. This prevents used cleaning fluid, i.e. waste fluid, from flowing back into the cleaning fluid feed line and contaminating the periodontal cleaning device. Thus hygiene is safeguarded. The first controllable valve can be controlled such that the fluid flow pulse is generated when there is sufficient pressure in the cleaning fluid supply. This allows a generate a sharp cleaning fluid pulse. In combination with a fluid pump, the first controllable valve can be activated shortly after activating the fluid pump.

In an embodiment, the cleaning fluid source comprises a cleaning fluid container. This allows standalone usage of the periodontal cleaning device. In use periodontal cleaning device does not need to be connected to a cleaning fluid supply and is therefore portable.

In an embodiment, the controllable suction means comprise a fluid suction pump. This allows a vacuum to be created in the suction member and remove waste fluid and sucked in air from the suction member, whilst the waste fluid can be drained freely from the periodontal cleaning device without a need to maintain a vacuum in the drain side of the pump. Thus reliability of the periodontal cleaning device is increased.

In an embodiment, the suction line comprises a second controllable valve between the controllable suction means and the suction member. The second controllable valve is arranged to allow flow of waste fluid and air only when sufficient underpressure is present at a controllable suction means side of the valve. This prevents waste fluid from entering the controllable suction means when the periodontal cleaning device is unused, i.e. not in action. Thereby hygiene of the periodontal cleaning device is improved. The second controllable valve can be controlled such that the vacuum pulse is generated when there is sufficient underpressure in the suction line. This allows a generate a sharp vacuum pulse. In combination with a vacuum pump, the second controllable valve can be activated shortly after activating the vacuum pump. Alternatively, when vacuum or underpressure is applied via the waste fluid drain, the required vacuum pulse can be generated by the second controllable valve alone.

In an embodiment, the suction line comprises a filter between the suction member and the controllable suction means. This prevents particles trapped in the filter in the waste fluid to enter the controllable suction means. Thus clogging and wear of the controllable suction means is prevented, providing longevity for the periodontal cleaning device.

In an embodiment, the periodontal cleaning device further comprises a waste fluid container connected to the controllable suction means. This also allows standalone usage of the periodontal cleaning device. In use periodontal cleaning device does not need to be connected to a waste fluid drain, and is therefore portable.

The object is also achieved in a method of controlling a periodontal cleaning device as described above, wherein the method of controlling the periodontal cleaning device is performed outside a subject's mouth. The method comprises controlling the controllable suction means in generating a vacuum pulse in the suction member, controlling the controllable fluid feeding means in generating a cleaning fluid flow pulse in the fluid outlet in response to the vacuum pulse, and controlling the controllable suction means in generating a subsequent vacuum pulse in the suction member. The controllable suction means are controlled to introduce a step of pausing a predetermined time period between the cleaning fluid flow pulse and the subsequent vacuum pulse in the suction member is introduced.

In an embodiment, the controlling the fluid feed means in generating a fluid flow pulse in the fluid outlet is performed in response to the vacuum pulse after the generating of a vacuum pulse.

The invention will be elucidated using the drawings set out below.

BRIEF DESCRIPTION OF THE DRAWINGS

It is noted that the drawings are only schematic and are not drawn to scale, unless otherwise stated. Same reference numbers have been used for same elements in different embodiments where possible.

DETAILED DESCRIPTION OF EXEMPLARY EMBODIMENTS OF THE INVENTION

Figure 1:
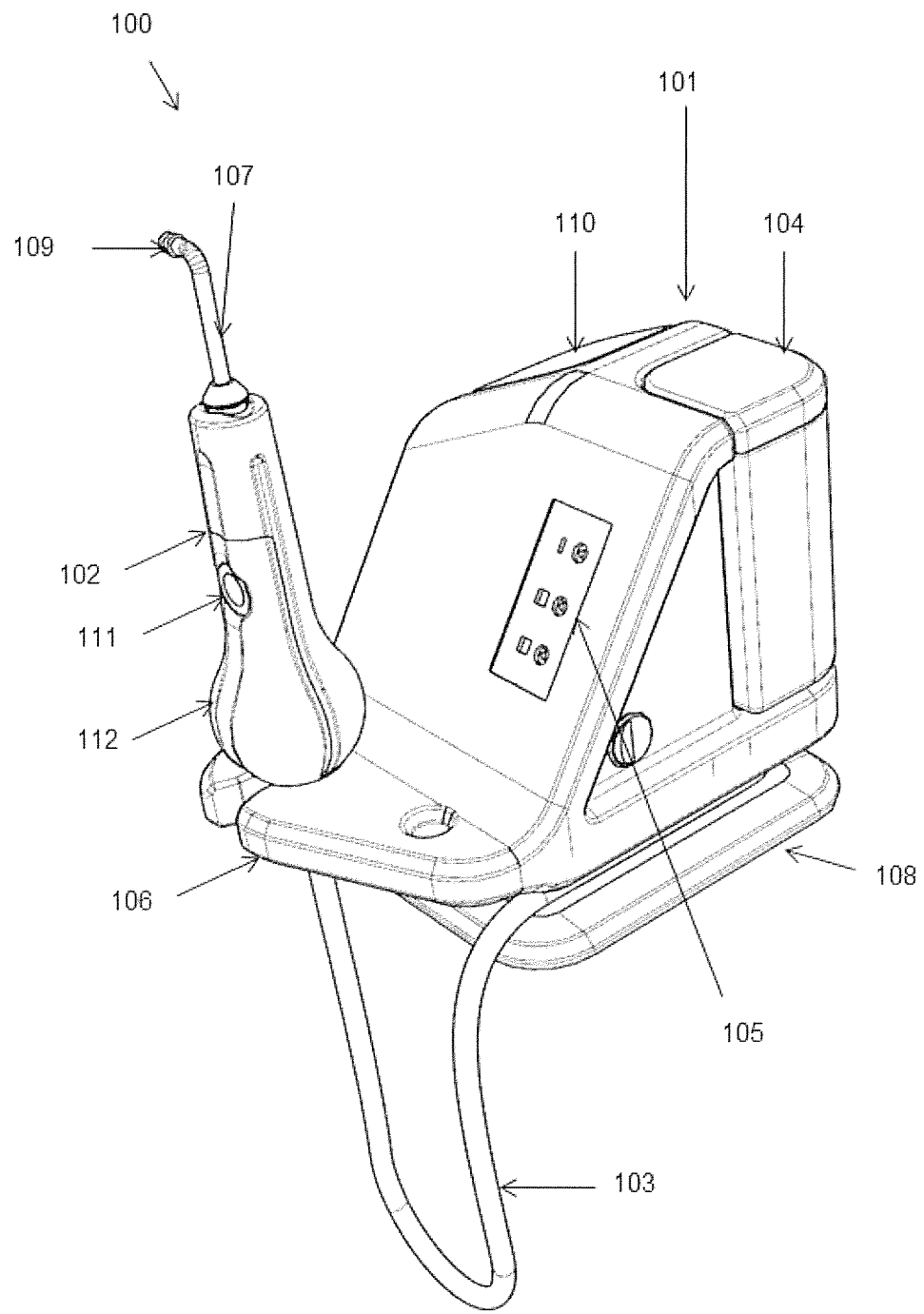
FIG. 1 shows a perspective view of the periodontal cleaning device according to an embodiment of the invention.

FIG. 1 shows a periodontal cleaning device 100 having an operating member 102 which is connect to a base station 101 via hose 103. In the example of FIG. 1, the base station 101 has a cleaning fluid container 104, operating controls 105, an operating member holder 106 and a base 108 on which the base station 101 is mounted.

A base station 101 can for example swivel around a central axle connecting the base 108 to the base station 101.

The operating member 102 has a handle 112 and a cleaning head 107. The operating member 102 can be provided with an operating control 111 for activating the periodontal cleaning device, i.e. the operating member 102.

The cleaning head 107 has at its far end a suction member 109, which can be applied to a subjects gums in the subjects mouth to perform periodontal cleaning. The applying of the suction member 109 can be performed by an operator or user of the periodontal cleaning device by holding the operating member by its handle and positioning the suction head 109 in a location of the subjects mouth for cleaning. The suction member 109 is designed for both applying a vacuum or low pressure to a subjects gums and subsequently discharging a cleaning fluid to the subjects gums. A subsequent new vacuum allows the discharged cleaning fluid, now waste fluid to be sucked in and a new vacuum to be created for a new cycle.

The hose 103 is provided with a suction channel and a cleaning fluid channel. Moreover the hose 103 can be provided with control wiring (not shown) for allowing an operator to control the periodontal cleaning device 101 using the operating control 111.

Figure 2A:
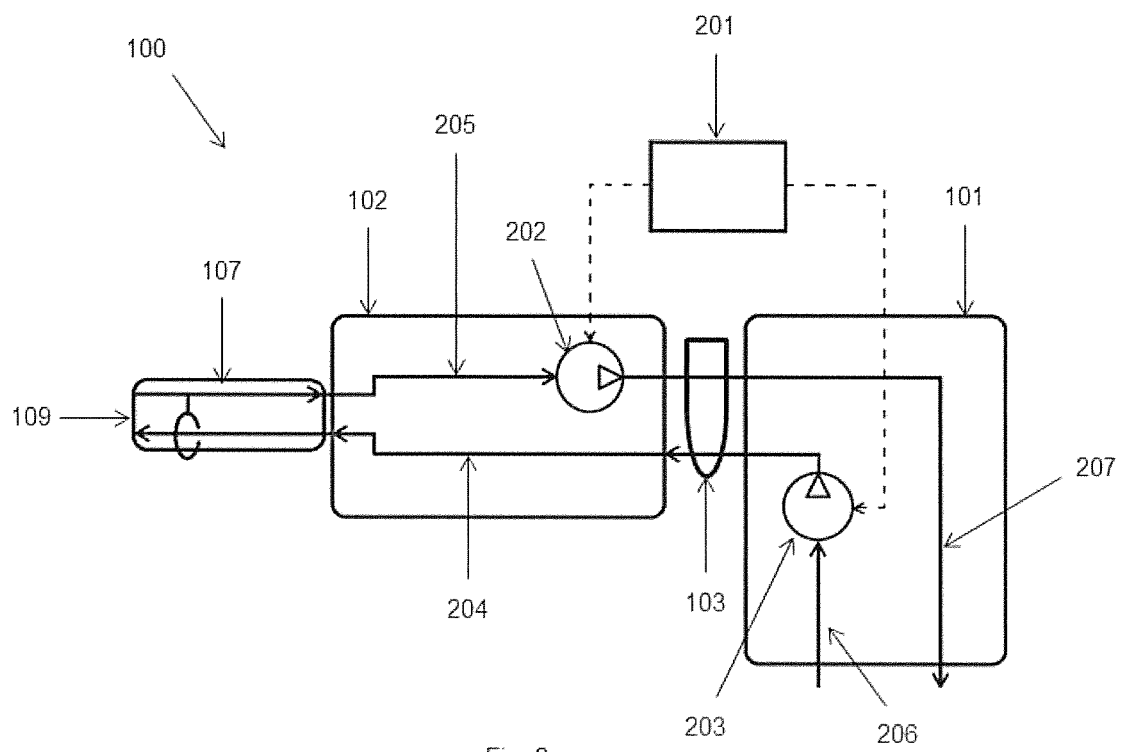
FIG. 2a shows a schematic diagram of the periodontal cleaning device according to an embodiment of the invention.

In the schematic diagram of FIG. 2a, the periodontal cleaning device 100 is represented in its simplest form. In this example a controllable fluid feeding means 203 is shown which is arranged for starting and stopping a supply of cleaning fluid from a cleaning fluid supply 206 to the cleaning fluid channel 204 through the hose 103, the operating member 102 and cleaning head 107 up to the suction member 109, where it is discharged into the subjects mouth. The controllable fluid feeding means 203 can for example be a valve, which can be switched on and off alternatingly by control unit 201. In that case, the cleaning fluid can be supplied from outside the periodontal cleaning device via the supply line 206 under outside pressure. Alternatively, the controllable fluid feeding means 203 is a cleaning fluid pump, which allows suction of the cleaning fluid via supply line 206 and pumping into the cleaning fluid channel 204. Using a cleaning fluid pump, the cleaning fluid need not be pressurized externally to reach the suction member 109.

Suction in the suction head 109 of the cleaning head 107 can be achieved through suction line 205 by applying low pressure to the waste fluid drain 207. The controllable suction means 202 can in this example be a vacuum valve, which can be intermittently controlled to apply the vacuum of the waste drain line 207 to the suction line 205 under control of the control unit 201. Air and/or waste fluids in waste fluid line 207 can be drained outside the base station 101. The skilled person will know various solutions for separating waste fluid from sucked in air.

The controllable suction means 202 is preferably a suction pump, capable of sucking in air and/or waste fluid from the suction member 109 and suction line 205. The suction pump 202 pumps the waste fluid and sucked in air in the waste fluid drain 207. The waste fluid from the suction line 205 and sucked in air can easily be disposed in or outside the base station 101. The suction pump can for example be a membrane pump.

Figure 2B:
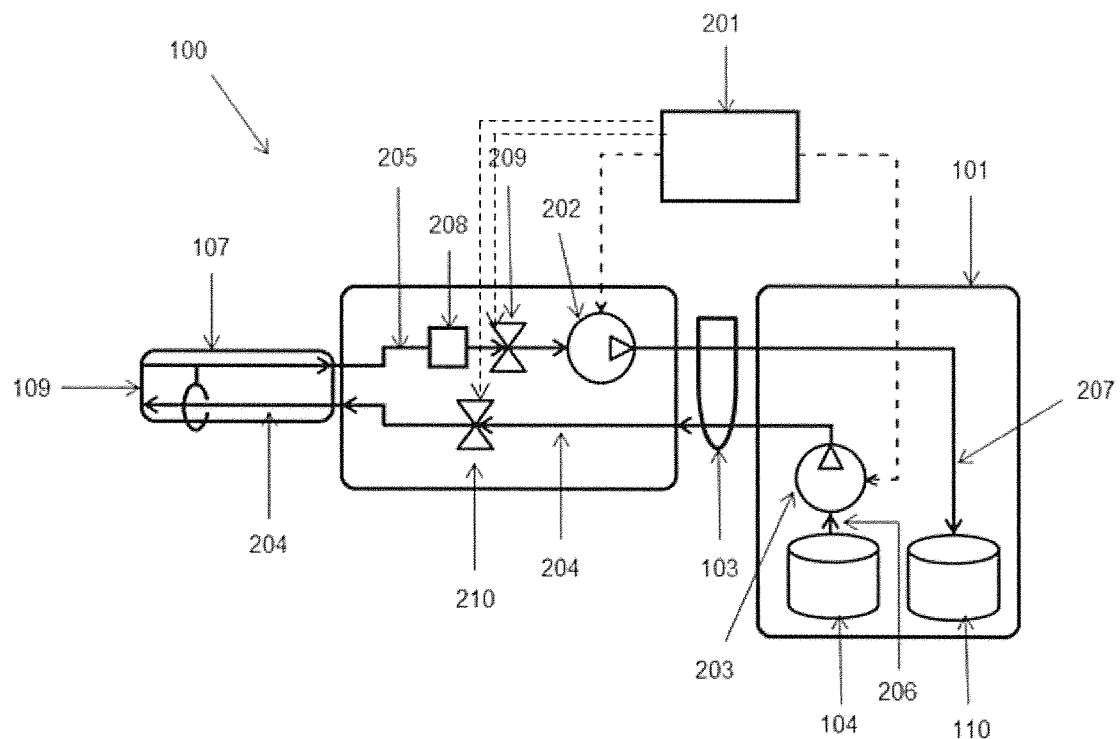
FIG. 2b shows a schematic diagram of the periodontal cleaning device according to another embodiment of the invention.

In FIG. 2b a more detailed example of a periodontal cleaning device is shown schematically. The base station 101 of the example of FIG. 2b has a cleaning fluid container 104 and a waste fluid container 110. This allows the periodontal cleaning device 100 to be used as a stand-alone device, independent from cleaning fluid supply or waste fluid drainage. The controllable fluid feeding means 203 is in this example the cleaning fluid pump as described under FIG. 2a. In the cleaning fluid supply line 204 a controllable valve 210 is preferably included for sharply switching on and off a cleaning fluid supply in supply line 204. This controllable valve 210 can be timed by the control unit 201 such that the controllable valve 210 is opened slightly after starting pump 203, to compensate for startup delay of the pump 203.

Similarly a controllable suction valve 209 can be included in the suction line 205. This controllable suction valve 209 can compensate for startup delay of the suction pump 202, which is required for this embodiment. The controllable suction valve 209 allows for sharp application of vacuum, i.e. suction in the suction line 205 and subsequently in the suction member 109. The controllable suction valve 209 is controlled simultaneously with the suction pump 202 by control unit 201.

The skilled person will recognize that localization of the suction pump 202, the controllable suction valve 209, the cleaning fluid pump 203 and cleaning fluid valve 210 in the operating member 102 and/or base station 101 is arbitrary. These parts can be accommodated in both parts 101, 102 of the periodontal cleaning device.

The control unit 201 is shown detached from the base station 101 and operating member 102, however the skilled person will understand that this control unit 201 can be accommodated in either of the parts 101, 102 of the periodontal cleaning device or outside of the base station 101.

A filter 208 may be introduced in suction line 205 to prevent larger particles to enter controllable valve 209 and/or suction pump 202. The filter 208 is removable and/or cleanable for maintenance.

Figure 2C:
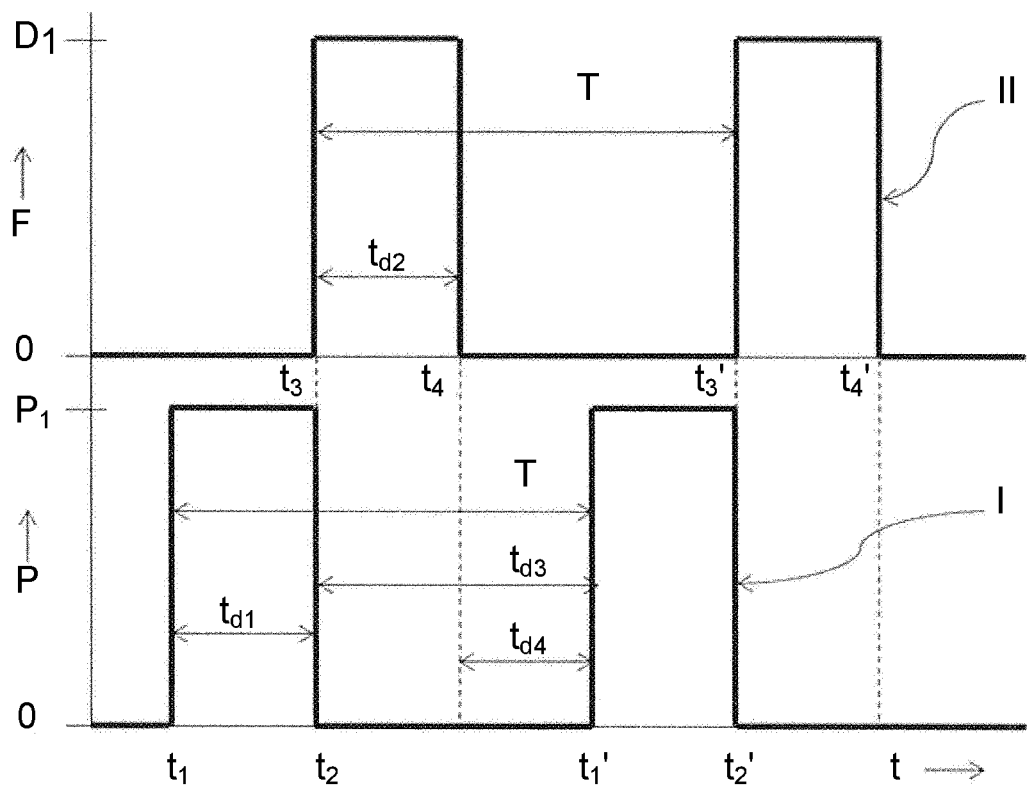
FIG. 2c shows a timing diagram of operating the periodontal cleaning device according to an embodiment of the invention.

In FIG. 2c a timing diagram is shown for controlling the controllable suction means 202 and/or the vacuum valve 209, see curve I. A vacuum with negative pressure or underpressure $P_1$ is to be generated in a periodic pulse like manner, having a period time T and a duty cycle determined by pulse width $t_{d1}$ and pause $t_{d3}$ until the next vacuum pulse. In curve I the vertical axis shows a negative pressure in the direction of the arrow for pressure P. In curve I a pressure 0 means atmospheric pressure, whilst $P_1$ means a vacuum or negative pressure relative to the atmospheric pressure. The negative pressure as shown in FIG. 2c is considered to be present in the suction line 205, whilst the fluid flow is considered to be present in the cleaning fluid feed line 204.

After ending the vacuum pulse at $t_2$, a cleaning fluid flow pulse is started at time $t_3$ as shown in curve II. Curve II depicts cleaning fluid flow F. The cleaning fluid flow pulses have a debit of $D_1$ microL per second. Time $t_3$ may coincide with $t_2$ or be shortly after $t_2$. The cycle time T is in a range of approximately 0.5 s to 1.5 s. Preferably the cycle time T is approximately 0.75 s. The pulse width $t_{d1}$ of the vacuum pulse and the pulse width of the cleaning fluid flow pulse $t_{d2}$ is preferably in the order of 0.25 s.

After ending the supply of cleaning fluid at time $t_4$, a pause with length $t_{d4}$ is introduced until $t'_1$ which marks the beginning of a new cycle, i.e. from time $t'_1$ the whole cycle repeats itself with period time T.

The vacuum P1 generated by the controllable suction means 202 in the suction line 205 is in the order of 25 to 50 mmHg. Preferably the vacuum is 35 mmHg. Moreover the amount of cleaning fluid produced in cleaning fluid feed line 204 is in the order of 50 to 200 microL. Preferably the amount of cleaning fluid is 90 microL.

Figure 3A:
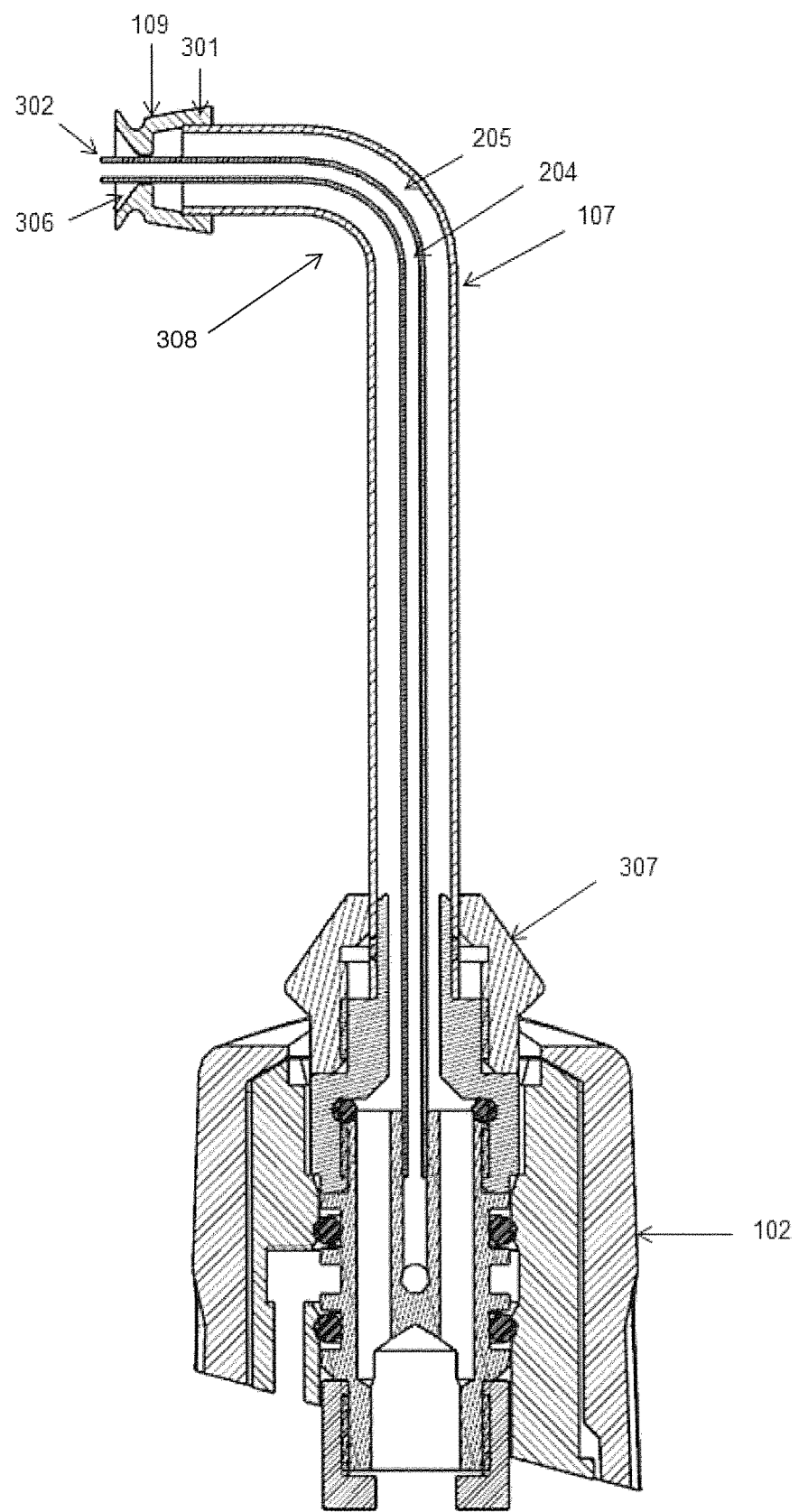
FIG. 3a shows a cleaning head of the periodontal cleaning device according to the embodiment of the invention.

In FIG. 3a the cleaning head 107 is shown in more detail. The cleaning head 107 is mounted for example by means of a nut 307 to the handle 112. The cleaning fluid feed line 204 is coaxially arranged within the suction line 205. In this example, the suction line 205 forms the outer wall of the cleaning head 107. Alternatively the suction line 205 and cleaning fluid feed line 204 may be incorporated within an outer sheath forming the cleaning head 107. The cleaning fluid feed line 204 can extend through the cleaning head to within the handle 111 to be connected to the suction pump 202 and or filter 208 at the end of the cleaning head 107 suction member is attached to the outer end of suction line 205 for example by clamping the suction member edge 301. In FIG. 3a the cleaning fluid feed line 204 is shown having tip 302 extending through the suction member 109. The suction member 109 is formed such that the cup is formed around the cleaning fluid feed line tip 302 to facilitate the forming of a vacuum at a subject's gum at which the suction member 109 is placed. The suction member 109 can be mounted on the cleaning head for example by clamping its rim 301 on the cleaning head end. Various ways of mounting the suction member are available to the skilled person.

Figure 3B:
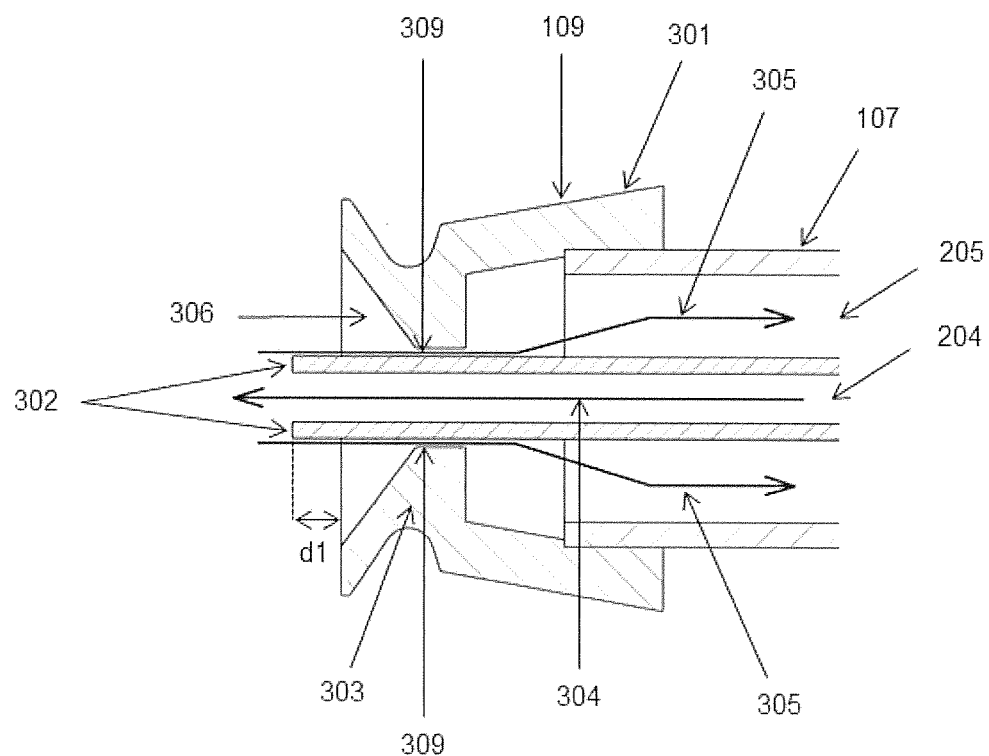
FIG. 3b shows a cross section of a suction member of the periodontal cleaning device according to the embodiment of the invention.

FIG. 3b shows a suction member 109 attached to suction line 205. The suction member 109 has an inward curved collar 303 which acts as support for the cleaning fluid feed line 204 extending through the suction member 109 and which ends in the tip 302. The collar 303 inner diameter is chosen relative to the cleaning fluid feed line 204 outer diameter such that a passage 309 for sucked in air and/or waste fluid is created. The passage 309 allows a vacuum to be built within suction member cup 306 and air and/or waste fluid to enter the suction member 109 and cleaning head 107 as shown by arrows 305. A discharge direction of the cleaning fluid from the cleaning fluid feed line 204 is shown by arrow 304.

Furthermore, the cleaning feed line 204 is dimensioned such that the tip 302 extends from the suction member 109 out of the suction cup 306 by a distance d1 when the suction member 109 is not yet applied to a subject's gum. This allows the cleaning fluid feed line tip 302 to act as a tactile instrument for the subject to establish a sensitive gum area in the subject's mouth.

Figure 3C:
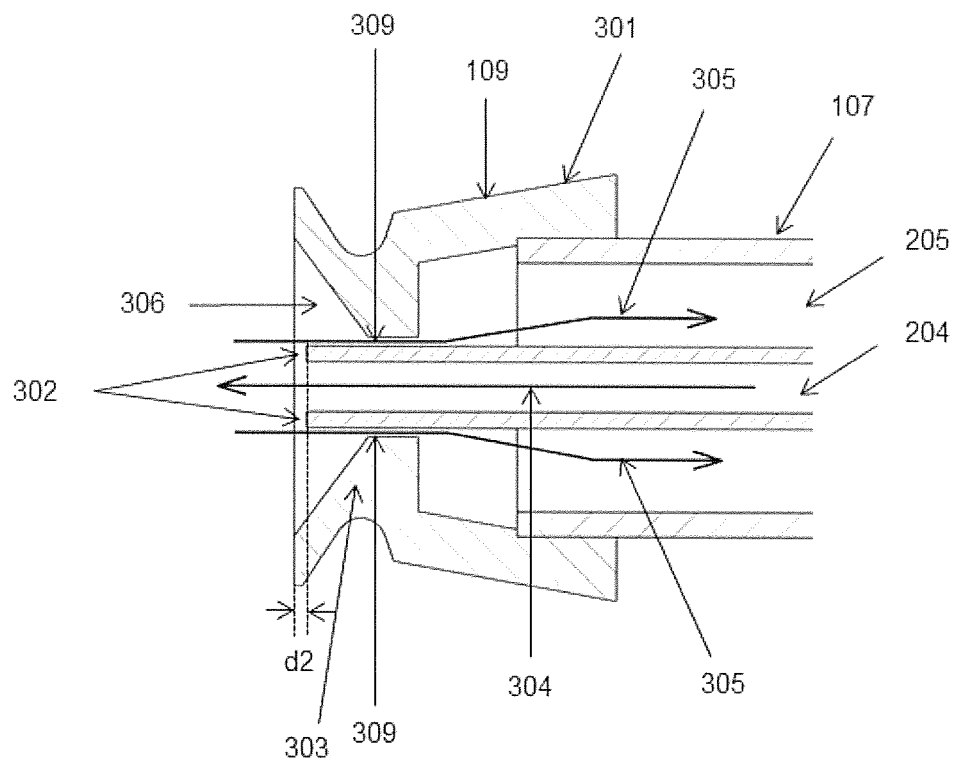
FIG. 3c shows a cross-section of the suction member of the periodontal cleaning device according to the embodiment of the invention.

In FIG. 3c is shown that the tip 302 can be pushed inside the suction member 109 with a distance d2 when the suction cup 306 is applied to the subject's gum. This achieved by manufacturing the cleaning fluid feed line 204 from resilient material and applying sufficient tolerances within the suction line 205 such that the cleaning fluid feed line tip 302 can easily be moved hence and forth within the suction member collar 303.

The suction member 109 is preferably made from soft, resilient material such as rubber, silicone rubber or like materials. This allows application of the suction member to be applied to a subject's gum without causing irritation or pain.

The above embodiments are described by way of example only. Variations thereof are possible without departing from the scope of protection as defined by the claims set out below.

REFERENCE NUMERALS 100 periodontal cleaning device
101 base station
102 operating member
103 connection hose
104 cleaning fluid container
105 operating controls
106 cleaning head holder
107 cleaning head
108 base
109 suction member
110 waste fluid container
111 operating control
112 handle
201 control unit
202 controllable suction means (202)
203 controllable fluid feeding means
204 cleaning fluid feed line
205 suction line
206 cleaning fluid supply
207 waste fluid drain
208 filter
209 controllable suction valve
210 controllable cleaning fluid feed valve
301 suction member rim
302 fluid outlet tip
303 suction element collar
304 cleaning fluid feed direction
305 waste fluid suction direction
306 suction cup
307 nut
308 bend
309 suction opening
d1 fluid outlet extension distance
d2 fluid outlet retraction distance
I vacuum pulse
II cleaning fluid flow pulse
$t_{d4}$ pause

What is claimed is:

1. A periodontal cleaning device, comprising:
an operating member including a cleaning head having a fluid outlet for releasing a cleaning fluid and a suction member for suction of a waste fluid, wherein the cleaning head is configured to be applied to periodontal areas of a subject's mouth including the crevices between teeth and gums, onto pockets that require cleaning;
a cleaning fluid source, connected to the fluid outlet via a fluid feed line;
a controllable suction means connected to the suction member via a suction line, wherein the suction member is made from soft, resilient material that can be applied to the subject's gums without causing pain or irritation;
controllable fluid feeding means for controlling a flow of the cleaning fluid from the cleaning fluid source to the fluid outlet;
a control unit, the control unit being arranged for:
controlling the controllable suction means in generating a vacuum pulse in the suction member;
controlling the controllable fluid feeding means in generating a cleaning fluid flow pulse in the fluid outlet in response to the vacuum pulse, and
controlling the controllable suction means in generating a subsequent vacuum pulse in the suction member;
wherein the control unit is arranged for pausing a predetermined time period between the generating the cleaning fluid flow pulse in the fluid outlet and the generating the subsequent vacuum pulse in the suction member,
wherein the fluid outlet for releasing the cleaning fluid is coaxially centered within the suction member,
wherein the suction member has a suction cup and a passage for sucked in air and/or waste fluid,
wherein the suction member is formed such that the cup is formed around the fluid outlet; and
wherein the suction line comprises a controllable valve between the controllable suction means and the suction member, wherein the control unit is arranged for controlling the controllable valve for generating the vacuum pulse in the suction member, and wherein the controllable valve is arranged in the operating member.

2. The periodontal cleaning device according to claim 1, wherein the fluid outlet resiliently extends beyond the suction member.

3. The periodontal cleaning device according to claim 1, wherein the predetermined time period is in a range of 150 to 500 ms.

4. The periodontal cleaning device according to claim 1, wherein the control unit is arranged for generating the cleaning fluid flow pulse in the fluid outlet in response to the vacuum pulse between the generating of the vacuum pulses.

5. The periodontal cleaning device according to claim 1, wherein the generating the cleaning fluid flow pulse involves generating a predetermined amount of cleaning fluid.

6. The periodontal cleaning device according to claim 1, wherein controllable fluid feeding means comprise a fluid pump between the cleaning fluid source and the fluid outlet.

7. The periodontal cleaning device according to claim 1, wherein the controllable fluid feeding means comprise a first controllable valve between the cleaning fluid source and the fluid outlet.

8. The periodontal cleaning device according to claim 1, wherein the cleaning fluid source comprises a cleaning fluid container.

9. The periodontal cleaning device according to claim 1, wherein the controllable suction means comprise a fluid suction pump.

10. The periodontal cleaning device according to claim 1, wherein the controllable valve is arranged to allow flow of waste fluid and air only when sufficient underpressure is present at the controllable suction means side of the controllable valve.

11. The periodontal cleaning device according to claim 1, wherein the suction line comprises a filter between the suction member and the controllable suction means.

12. The periodontal cleaning device according to claim 1, further comprising a waste fluid container connected to the controllable suction means.

13. The periodontal cleaning device according to claim 1, wherein the predetermined amount of cleaning fluid is in the order of 50 to 250 microL.

14. A method of controlling a periodontal cleaning device comprising:
an operating member including a cleaning head having a fluid outlet for releasing a cleaning fluid and a suction member for suction of a waste fluid, wherein the cleaning head is configured to be applied to periodontal areas of a subject's mouth including the crevices between teeth and gums, onto pockets that require cleaning;
a cleaning fluid source, connected to the fluid outlet via a fluid feed line;
a controllable suction means connected to the suction member via a suction line, wherein the suction member is made from soft, resilient material that can be applied to the subject's gums without causing pain or irritation;
controllable fluid feeding means for controlling a flow of the cleaning fluid from the cleaning fluid source to the fluid outlet;
a control unit, the control unit being arranged for:
controlling the controllable suction means in generating a vacuum pulse in the suction member;
controlling the controllable fluid feeding means in generating a cleaning fluid flow pulse in the fluid outlet in response to the vacuum pulse, and
controlling the controllable suction means in generating a subsequent vacuum pulse in the suction member;
wherein the control unit is arranged for pausing a predetermined time period between the generating the cleaning fluid flow pulse in the fluid outlet and the generating the subsequent vacuum pulse in the suction member,
wherein the fluid outlet for releasing the cleaning fluid is coaxially centered within the suction member,
wherein the suction member has a suction cup and a passage for sucked in air and/or waste fluid,
wherein the suction member is formed such that the cup is formed around the fluid outlet, and
wherein the suction line comprises a controllable valve between the controllable suction means and the suction member, wherein the control unit is arranged for controlling the controllable valve for generating the vacuum pulse in the suction member, and wherein the controllable valve is arranged in the operating member,
wherein the method of controlling the periodontal cleaning device is performed outside a subject's mouth, the method comprising the steps of:
controlling the controllable suction means in generating the vacuum pulse in the suction member;
controlling the controllable fluid feeding means in generating the cleaning fluid flow pulse in the fluid outlet in response to the vacuum pulse;
controlling the controllable suction means in generating the subsequent vacuum pulse in the suction member; and
pausing the predetermined time period between the generating the cleaning fluid flow pulse in the fluid outlet and the generating the subsequent vacuum pulse in the suction member,
and wherein the controlling the controllable suction means in generating the vacuum pulse in the suction member and the subsequent vacuum pulse in the suction member comprises controlling the controllable valve in the operating member.

15. The method according to claim 14, wherein the controlling the fluid feed means in generating the cleaning fluid flow pulse in the fluid outlet is performed in response to the vacuum pulse after the generating of the vacuum pulse.

16. The method according to claim 14, wherein the predetermined time period is in a range of 150 to 500 ms.

17. The method according to claim 14, wherein the generating the cleaning fluid flow pulse involves generating a predetermined amount of cleaning fluid.

18. The method of claim 14, wherein the controlling the controllable suction means in generating the vacuum pulse in the suction member and the subsequent vacuum pulse in the suction member comprises controlling the controllable valve in the operating member only when sufficient underpressure is present at the controllable suction means side of the controllable valve.

19. The method of claim 17, wherein the predetermined amount of cleaning fluid is in the order of 50 to 250 microL.

20. A periodontal cleaning device, comprising:
a cleaning head having a fluid outlet for releasing a cleaning fluid and a suction member for suction of a waste fluid, wherein the cleaning head is configured to be applied to periodontal areas of a subject's mouth including the crevices between teeth and gums, onto pockets that require cleaning;
a cleaning fluid source, connected to the fluid outlet via a fluid feed line;
a controllable suction means connected to the suction member via a suction line, wherein the suction member is made from soft, resilient material that can be applied to the subject's gums without causing pain or irritation;

controllable fluid feeding means for controlling a flow of the cleaning fluid from the cleaning fluid source to the fluid outlet;

wherein the suction member has a suction cup and a passage for sucked in air and/or waste fluid, and wherein the suction member is formed such that the cup is formed around the fluid outlet;

and wherein the periodontal cleaning device further comprises a control unit, the control unit being arranged for:

controlling the controllable suction means in generating vacuum pulses in the suction member;

controlling the controllable fluid feeding means in generating a cleaning fluid flow pulses in the fluid outlet;

the control unit being arranged for controlling the controllable suction means and the controllable fluid feeding means in an alternating manner to generate a cleaning fluid flow pulse in the outlet and a repeating cycle comprising:

a vacuum pulse in the suction member that begins after an end of the cleaning fluid flow pulse or an end of a subsequent cleaning fluid flow pulse, respectively, and after pausing a predetermined time period wherein neither a vacuum pulse nor a cleaning fluid flow pulse is generated, and the subsequent cleaning fluid flow pulse beginning no later than a short time period after an end of the vacuum pulse, the short time period being shorter than the predetermined time period.

21. The periodontal cleaning device of claim 20, wherein the repeating cycle comprises the subsequent cleaning fluid flow pulse beginning coincident with the end of the vacuum pulse.

* * * * *